United States Patent
Brewer et al.

(10) Patent No.: US 11,039,770 B2
(45) Date of Patent: Jun. 22, 2021

(54) DRUG DETECTION DEVICE

(71) Applicants: Jonathan Brewer, Dallas, TX (US); Ali Elaydi, Cedar Hill, TX (US); Akhilesh Padhye, Highland Village, TX (US); Vitaliy Davidov, Houston, TX (US)

(72) Inventors: Jonathan Brewer, Dallas, TX (US); Ali Elaydi, Cedar Hill, TX (US); Akhilesh Padhye, Highland Village, TX (US); Vitaliy Davidov, Houston, TX (US)

( * ) Notice: Subject to any disclaimer, the term of this patent is extended or adjusted under 35 U.S.C. 154(b) by 357 days.

(21) Appl. No.: 15/925,041

(22) Filed: Mar. 19, 2018

(65) Prior Publication Data
US 2018/0263544 A1    Sep. 20, 2018

Related U.S. Application Data

(60) Provisional application No. 62/473,981, filed on Mar. 20, 2017.

(51) Int. Cl.
| | |
|---|---|
| *G01N 30/00* | (2006.01) |
| *A61B 5/15* | (2006.01) |
| *B01L 3/00* | (2006.01) |
| *G01N 33/98* | (2006.01) |
| *A61B 5/157* | (2006.01) |
| *G01N 33/94* | (2006.01) |

(52) U.S. Cl.
CPC ........ *A61B 5/150755* (2013.01); *A61B 5/157* (2013.01); *A61B 5/150022* (2013.01); *A61B 5/150343* (2013.01); *B01L 3/52* (2013.01); *G01N 33/98* (2013.01); *B01L 2300/041* (2013.01); *B01L 2300/046* (2013.01); *B01L 2300/0636* (2013.01); *B01L 2300/0672* (2013.01); *B01L 2300/0832* (2013.01); *B01L 2400/0406* (2013.01); *G01N 33/94* (2013.01)

(58) Field of Classification Search
CPC ........ G01N 21/6428; B01L 2300/0672; B01L 2400/0406
USPC ..................... 422/410, 412, 82.08
See application file for complete search history.

(56) References Cited

U.S. PATENT DOCUMENTS

| | | | | | |
|---|---|---|---|---|---|
| 3,848,581 | A | * | 11/1974 | Cinqualbre | ...... A61B 5/150236 600/575 |
| 2009/0118752 | A1 | * | 5/2009 | Perez | ............... A61B 5/150358 606/181 |

* cited by examiner

*Primary Examiner* — Natalia Levkovich (57) ABSTRACT

In a first aspect, there is a device for detecting a substance within blood, including a collecting tube dimensioned to draw in blood through capillary action; a reagent chamber containing a reactive element; and a connector tube providing fluid communication between the reagent chamber and the collecting tube; wherein the connector tubes are dimensioned to draw in blood through capillary action to the reagent chamber. In other aspects, the device can include an outer casing and/or a plurality of reagent chambers each with a reactive element therein.

21 Claims, 7 Drawing Sheets

DRUG DETECTION DEVICE

CROSS-REFERENCE TO RELATED APPLICATION

This application claims priority to U.S. provisional patent application No. 62/473,981, filed Mar. 20, 2017, all of which is hereby incorporated by reference for all purposes as if fully set forth herein.

BACKGROUND

Technical Field

The present application relates to a detection device that determines which substance (e.g., a drug) is in an overdose patient's bloodstream, and the appropriate life-saving measures that should be employed based on the substance identified.

Description of Related Art

First responders are currently limited in the way they evaluate an overdose, poisoning, and/or illness of a patient. First responders may be limited to evaluating a patient using basic life support treatments, such as assessing health emergencies by measuring vital signs and other symptoms. Based on what symptoms are present, first responders can either administer a drug to counteract the symptoms, or monitor the patient and quickly transport them to the hospital. This delay in implementing life-saving measures can have adverse, if not fatal, results. Based on the report of the first responder and the diagnosis of the admitting Emergency Room ("ER") doctor, another clinical judgment call has to be made on whether or not to delay life-saving treatment pending laboratory results. Waiting on the laboratory test results to come back can take up to thirty minutes after the patient is admitted to the ER, in addition to the time it took to reach the hospital. An undesired delay in treatment can have detrimental consequences on the state of the patient.

DESCRIPTION OF THE DRAWINGS

The novel features believed characteristic of the embodiments of the present disclosure are set forth in the appended claims. However, the embodiments themselves, as well as a preferred mode of use, and further objectives and advantages thereof, will best be understood by reference to the following detailed description when read in conjunction with the accompanying drawings, wherein:

DESCRIPTION OF THE PREFERRED EMBODIMENT

Illustrative embodiments of the testing device are described below. In the interest of clarity, all features of an actual implementation may not be described in this specification. It will, of course, be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the devices, members, apparatuses, etc. described herein may be oriented in any desired direction.

One conventional method for diagnosing which particular substance (e.g., drugs, poison) is in a person's bloodstream is most accurately determined after a person has been admitted to a hospital and a lab test is done on their blood. But there is not always time to wait for the results of the test to come back, which can take up to thirty minutes after a person is admitted to the hospital. Emergency Medical Technicians ("EMTs") and ambulances are typically outfitted with multiple types of drugs to counteract an overdose, but EMTs are limited in how they can diagnose the drug in which a patient overdosed on. Unless the person is awake and cooperative, which is not usually the case, the EMTs look at what symptoms are present, such as pupil size for example, by their normal means of examining a person. Based on the observable symptoms, EMTs determine the most likely substance the patient took and either administer the counteracting drug hoping they were correct, or monitor the patient's vitals and inform the admitting ER doctor who then makes a determination based on rechecking the patient while also ordering the lab test.

These conventional methods can lead to a misdiagnosis as to which drug a person took, which can have adverse effects on the patient, or lead to a longer time period before any type of life-saving measure is enacted. This longer time period can also have adverse effects on the patient or even lead to death because too much time elapsed.

In contrast, a method utilizing the device of the present disclosure has significant advantages over conventional methods because the device can be used to quickly ascertain the specific class of drug the patient may have used. The time period is drastically reduced to the small amount of time it takes for the device to determine the class of drug, for the EMT to grab the counteragent, and to administer the counteragent to the patient. While EMTs are specifically mentioned, the device is intended to be used by all first responders, such as firefighters and police officers to name a few. Furthermore, the device could be used by other medical personnel or even by a parent or guardian in diagnosing their child. One primary objective of the present application is to provide a device that will cut down on the current difficulty level and time needed to identify the drug present in the patient's bloodstream.

The embodiments of the device and method for use will be described with reference to a drug detection device for use with a drug overdose in a patient's bloodstream, it will be appreciated that the drug detection device may be used for other bodily fluids, for example, but not limitation, urine, mucous, etc. However, blood is preferred over other bodily fluids because blood has a predictable concentration, of a detectable substance (as opposed to the dilution and contamination problems that can occur with saliva and urine). Additionally, the detection devices and methods for use can be used to detect a wide variety of substances in blood including, but not limited to, at least one of the following: a drug, an active ingredient in a drug, an illicit drug, a narcotic drug, a prescription drug, an over-the-counter drug, opium, tetrahydrocannabinol (THC), synthetic cannabinoids, K2, phencyclidine (PCP), gaseous intoxication (e.g., carbon monoxide), toxins (e.g., botulism), alcohol, venom (venom from snakes, spiders, scorpions, etc.), amphetamine, lysergic acid diethylamide (LSD), acetaminophen, a hazardous chemical, a household chemical (e.g., bleach, detergent packets, anti-freeze, drain cleaner, etc.), a hazardous plant, a chemical weapon, a biological illness, a biological disease (e.g., a bacterial disease or infection), or a biological weapon.

In one example embodiment, the device contains up to five chemical crystalline reagents that will each chemically react to the presence of a different class of drug in the blood. If the specific class of drug is present, then the reagent will change color and be observable by the user. The device is designed to be highly functional in order to increase efficiency in identifying the drug in an overdose patient's bloodstream yet also be simple to manufacture.

Figure 1:
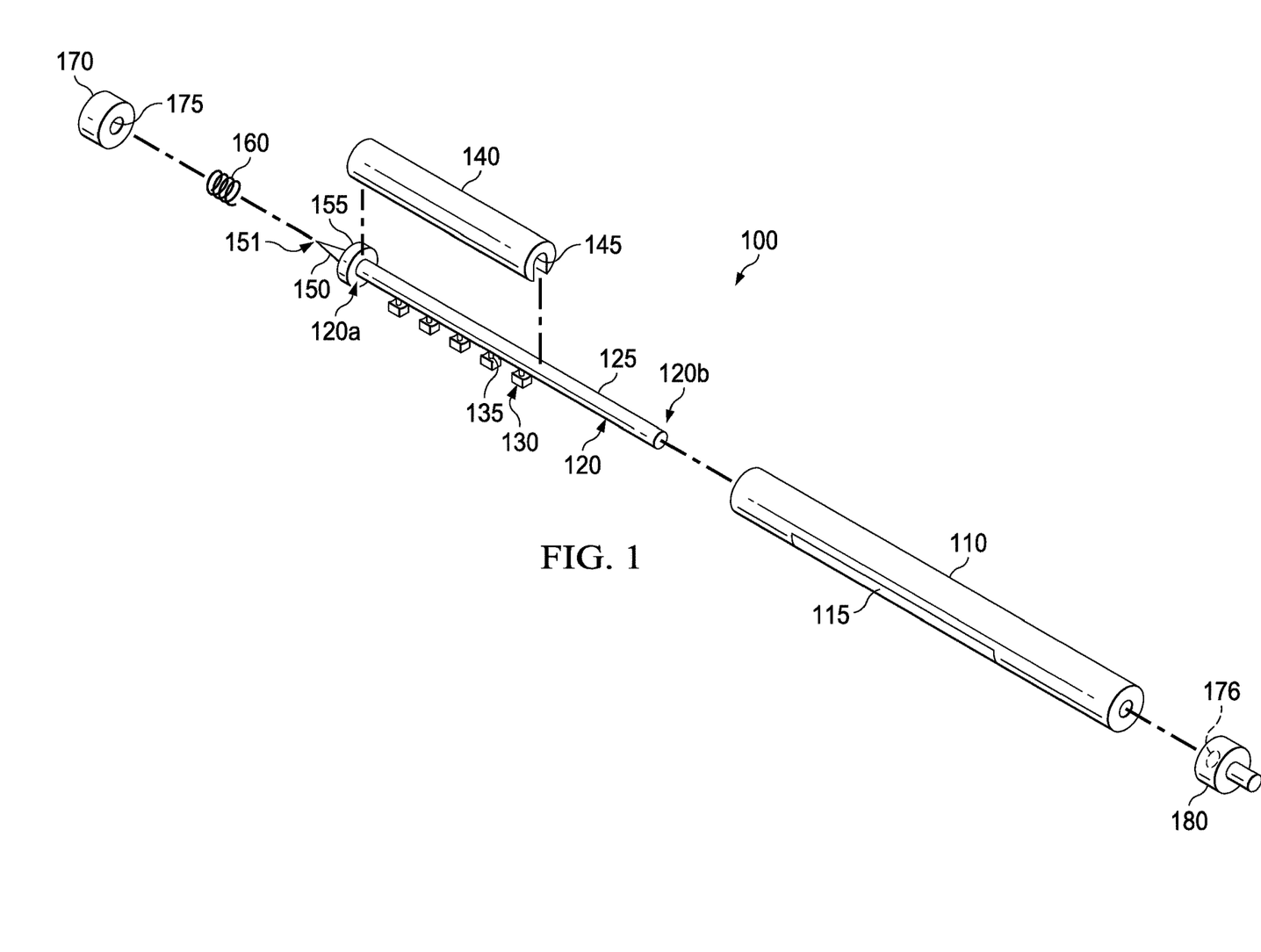
FIG. 1 is an exploded view of the of the drug detection device, according to one example embodiment.
Figure 4A:
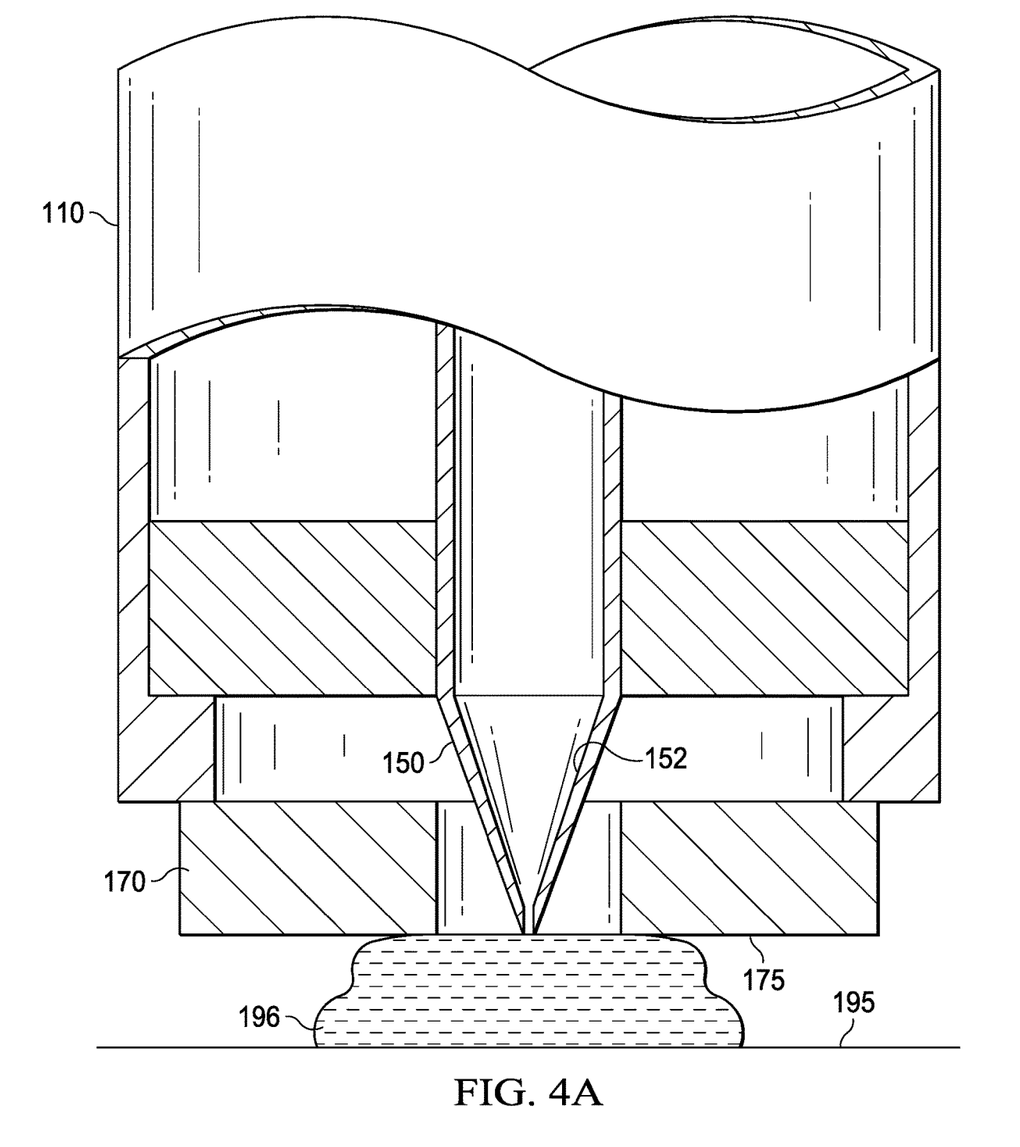
FIG. 4A is a partial broken-away view of a drug detection device with a hollow lancet, according to an illustrative embodiment.
Figure 4B:
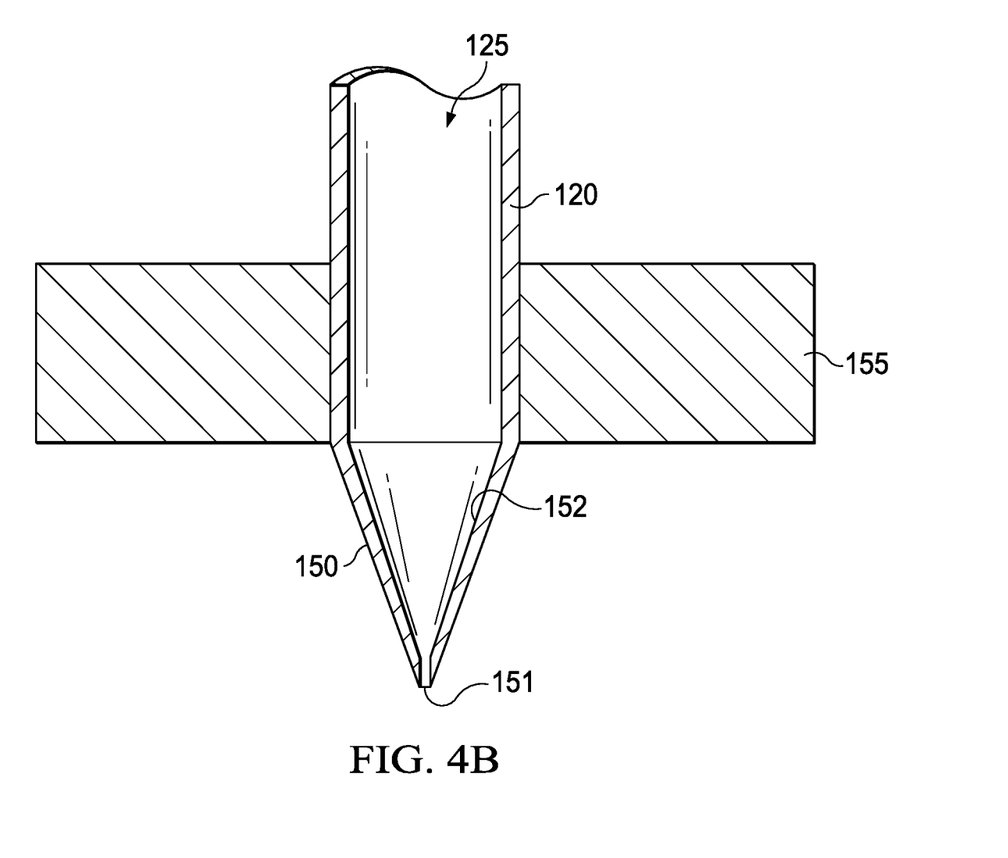
FIG. 4B is a cross-sectional view of a drug detection device with a hollow lancet, according to an exemplary embodiment.

Referring to FIGS. 1 and 4A-4B, detection device 100 is comprised of components that mechanically work together to draw blood from a patient and analyze the blood with reactive elements disposed in reagent chambers. Device 100 comprises an outer casing 110 that is diametrically disposed to house all the other elements with the reagent opening 115.

The collecting tube 120 has a hollow portion 125 that is configured for fluid travel. The collecting tube 120 has an entry opening 120 a where the blood from a patient enters therein and a top end 120 b opposite from the entry opening 120 a. The reagent chambers 130 are in fluid communication with the collecting tube 120 and hollow portion 125 through hollow connector tubes 135 that are also configured for fluid travel. Connector tubes 135 have a diameter smaller than a diameter of the collecting tube 120, as shown in FIGS. 3A-3F. The reagent chambers 130 are connected specifically to the collecting tube 120 so as to interact with the reagent opening 115 on the outer casing 110.

In an embodiment, an inner casing 140 is disposed within the outer casing 110. The inner casing 140 has an open section 145 such that the opening is diametrically disposed to fit around the reagent chambers 130 and the collecting tube 120. The inner casing 140 functions to stabilize the reagent chambers during operation.

A lancet striker can be included in the device 100. The lancet striker can include a top button 180, spring 160, cover 170, and lancet 150. The lancet 150 is located at the entry opening 120a of the collecting tube 120. A spring base 155 is disposed around where lancet 150 joins with the collecting tube 120. The tip 151 of the lancet 150 has an opening that leads to an inner hollow portion 152 of the lancet 150 that is connected to and is in fluid communication with the hollow portion 125 of collecting tube 120. Outer casing 110 has top button 180 inserted at one end for engaging the device 100 and cover 170 at the other end for protecting the sterility of the device 100. Spring 160 is disposed around lancet 150 and located between the spring base 155 and cover 170. Cover 170 has a cover opening 175 so that lancet 150 can interact with the patient once the device 100 is engaged.

Figure 2A:
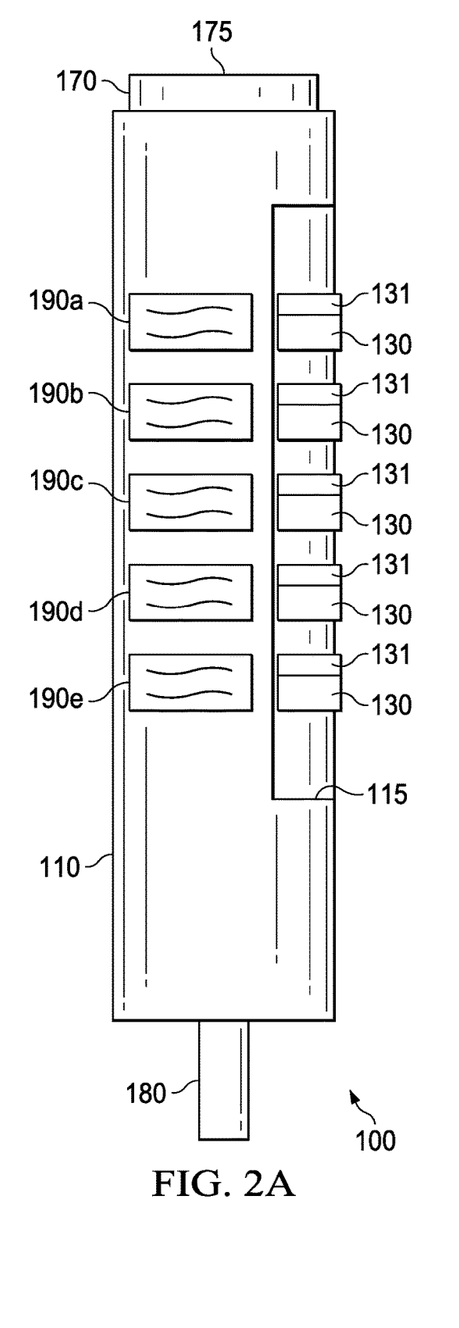
FIG. 2A is a side view of the drug detection device, according to one example embodiment.
Figure 2B:
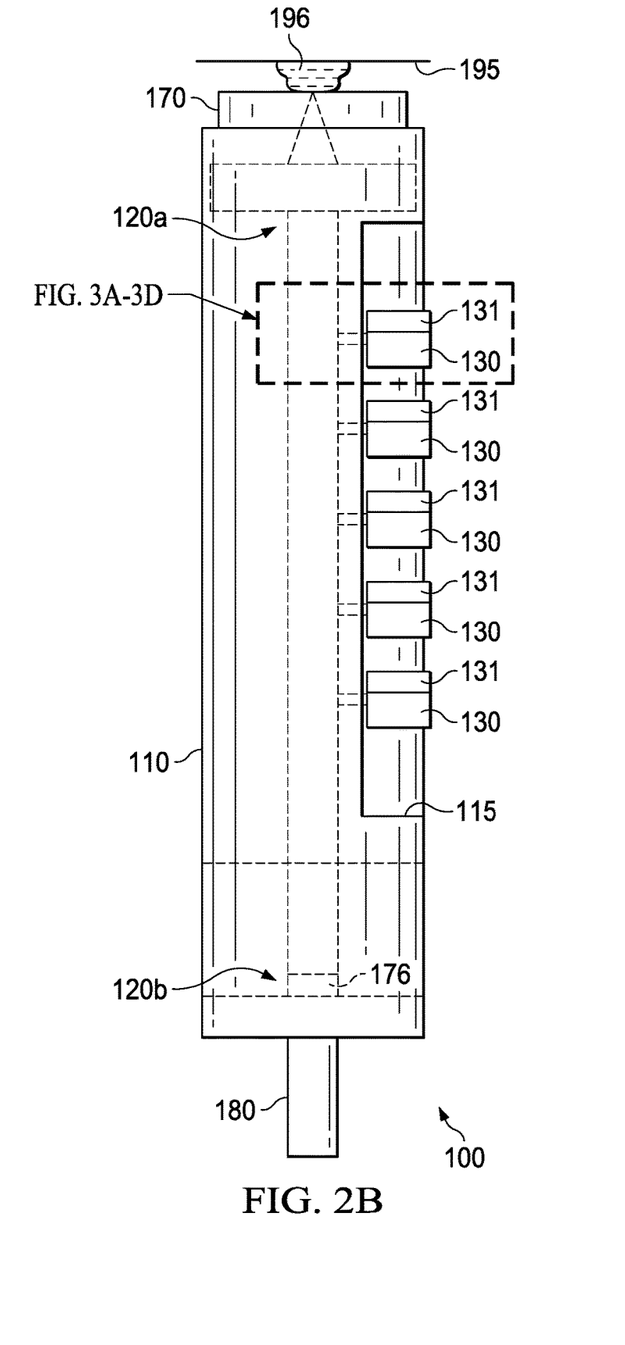
FIG. 2B is a cross-sectional view of the drug detection device before the device in FIG. 2A has been activated, according to one example embodiment.

FIGS. 2A-2B illustrate a partially stylized view of the detection device 100. In an embodiment, each of the reagent chambers 130 produces a different type of reaction from the other reagent chambers (e.g., one reagent chamber produces a green color, one reagent chamber produces a yellow color, one reagent chamber produces an orange color, etc.). For example, labels 190a-190e are located on the outer chamber 110 proximate each reagent chamber 130. Each label 190a-190e can include two lines of text to keep the process simple and help first responders identify which drug has been identified. The first line of text can identify the type of drug that the specific reagent chamber 130 is going to identify and the second line of text can identify which color the crystalline reagent will change to if that specific drug is located in the patient's bloodstream. By way of example, the first line of text of label 190a is "Opium" and the second line of text is "Dark Orange/Yellow." By way of example, the first line of text of label 190b is "Cocaine" and the second line of text is "Greenish-Blue." By way of example, the first line of text, of label 190c is "THC" and the second line of text is "Purplish-Blue." By way of example, the first line of text of label 190d is "Amphetamine" and the second line of text is "Reddish-Orange." By way of example, the first line of text of label 190e is "LSD" and the second line of text is "Yellow/Green." Another option for a potential label can be prescription or over-the-counter drug; for example, but not limitation, the first line of text is "Acetaminophen" and the second line to be "Blue." In an alternate embodiment, the labels 190a-190e are located on each reagent chamber 130 and can be viewed through the reagent opening 115. In another alternate embodiment, the labels 190a-190e are located on the inner casing 140 next to each reagent chamber 130 and can be viewed through the transparent outer chamber 110. In yet another embodiment, the outer casing 110 does not include the labels 190a-190e and a reference card with a color coding chart can be used (e.g., similar to a urine dipstick color chart).

Referring to FIG. 2B, the mechanically activated device 100 with the lancet 150 piercing the skin 195 is illustrated. During operation, device 100 is placed against the skin of the patient, usually against the muscle of the thigh, with the lancet 150 side against the skin. The device 100 is activated by pushing down on the top button 180. The mechanical force, tempered by the compression of the spring 160 between the cover 170 and the spring base 155, pushes the lancet 150 through the cover opening 175, which causes the lancet 150 to protrude from the device 100 and pierce the skin 195 of the patient. In one example embodiment, device 100 is configured so that the lancet 150 pierces the skin 195 to a depth of approximately one centimeter. After lancet 150 pierces the skin 195, top button 180 is released causing the spring 160 to decompress and the lancet 150 to retreat into the device 100.

The device 100 is designed so that the lancet 150 is near the cover opening 175. After the lancet 150 is withdrawn from the skin 195, the blood 196 wells and comes into contact with the cover opening 175 and lancet 150. Capillary forces cause the blood 196 of the patient to flow up through the opening in the tip 151 of the lancet 150, through the lancet 150, and into the hollow portion 125 of the collecting tube 120. As the blood 196 travels through the collecting tube 120, the blood 196 is drawn into each connector tube 135 by capillary forces and into each reagent chamber 130.

Figure 3A:
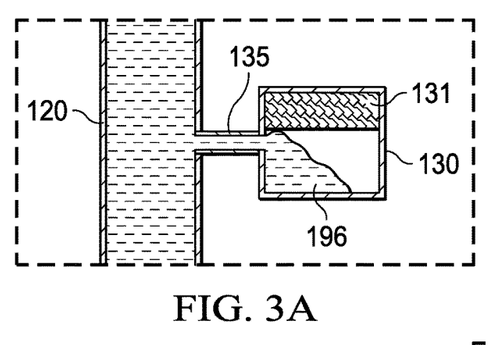
FIG. 3A is a cross-sectional view of a chemical testing chamber with a reactive element therein, according to one example embodiment.

The reagent chambers 130 are situated within the device 100 so that they are visible through the reagent opening 115 and the effect on one of the reagent chambers 130 is immediately observable. The reagent chambers 130 can be at least one of the following shapes: a cylinder, as shown in FIG. 3C; a cuboid; and a rectangular cuboid, as shown in FIG. 3A. It should be appreciated that other shapes and geometries can be used for the reagent chambers 130.

Figure 3B:
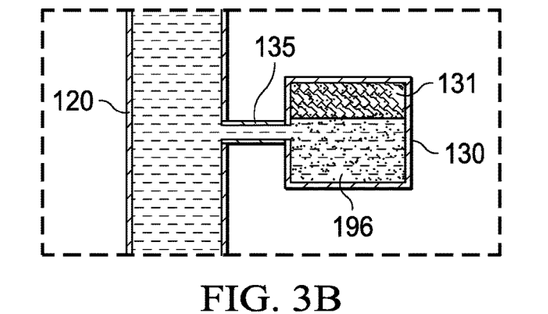
FIG. 3B is a cross-sectional view of a positive reaction for the chemical testing chamber in FIG. 3A, according to one example embodiment.
Figure 3C:
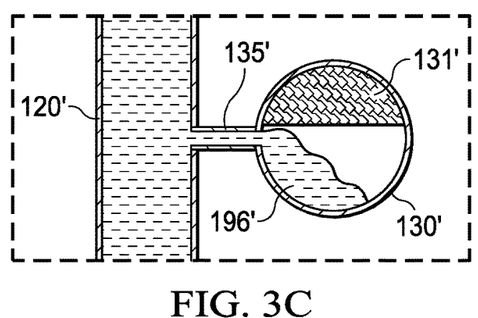
FIG. 3C is a cross-sectional view of one example embodiment of the chemical testing chamber with a reactive element therein, according to one example embodiment.
Figure 3D:
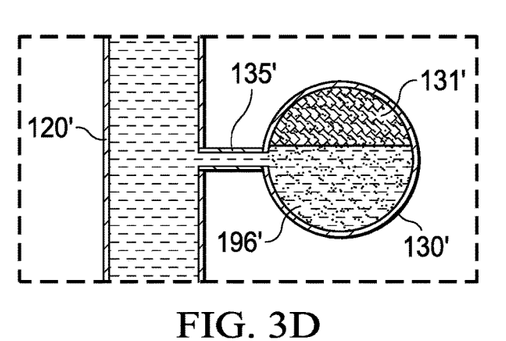
FIG. 3D is a cross-sectional view of a positive reaction for the chemical testing chamber in FIG. 3C, according to one example embodiment.
Figure 3E:
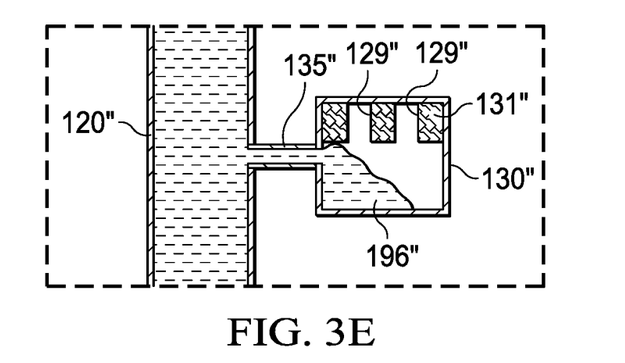
FIG. 3E is a cross-sectional view of one example embodiment of the chemical testing chamber with a reactive element therein, according to one example embodiment.

Referring to FIGS. 3A-3F, each reagent chamber 130 contains implementation specific reactive elements 131 that each interact with a specific drug and changes to a specific color as identified by each label 190a-190e located near each reagent chamber 130. Each of FIGS. 3A, 3C, and 3E illustrate the reagent chamber 130 with an exemplary reactive element 131, 131', 131" with blood entering the chamber 130 and contacting the respective reactive element therein. In an embodiment, the active element 131, 131' 131" is disposed adjacent to the connector tube 135 to elicit a positive reaction as the blood enters into the reagent chamber. In an embodiment, the reactive element 131 can be a crystalline reagent used for an immunoassay. In an embodiment, the crystalline reagent includes a tagged antibody that elicits a positive reaction. In some embodiments, the reactive element 131 is configured to provide a visible change in the reagent chamber that identifies a positive reaction to the substance (e.g., a change in color and/or a florescent glow). One advantageous feature of device 100 is that the crystalline form of the reactive element 131 prevents backflow because the individual crystals are larger than the diameter of the hollow connector tubes 135, which increases the specificity and sensitivity of the device 100.

In some embodiments, the reactive element 131 is secured to an inner surface of the reagent chamber 130. The reactive element 131 can be positioned in the reagent chamber 130 so that it is adjacent to the connector tube 135. The reactive element 131 adjacent to the connector tube 135 advantageously elicits a reaction with the reactive element 131 as soon as blood enters the reagent chamber 130 and does not require the reagent chamber to be full. In a preferred embodiment, as shown in FIGS. 3A and 3C, the reactive element 131 is secured to a top surface in the interior of the reagent chamber 130. In an exemplary embodiment, the reactive element 131 is secured to the reagent chamber 130 with an inert cement.

Figure 3F:
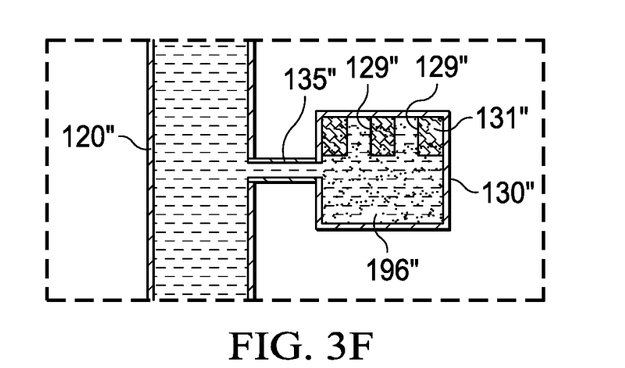
FIG. 3F is a cross-sectional view of a positive reaction for the chemical testing chamber in FIG. 3E, according to one example embodiment.

In exemplary embodiments, the reactive element 131 is a shape that compliments and fits into at a least a portion of the interior of the reagent chamber 130. For example, in FIGS. 3A-3B and 3E-3F, the reactive element 131, 131" is a rectangular cuboid shape that is positioned in the respective reagent chamber 130, 130". In another example as shown in FIGS. 3C-3D, the reactive element 131' is hemi-spherical in shape disposed within the cylindrical shaped reagent chamber 130'. In an embodiment, as shown in FIGS. 3E-3F, reactive element 131" includes a plurality of apertures 129" for receiving the blood 196 therein. In some embodiments, the plurality of apertures 129" permits a faster positive result due to the increased surface area and/or porosity of the reactive element 131" for reacting with blood 196.

Referring now to FIGS. 3B, 3D, and 3F, as each reactive element 131, 131', 131" interacts with the blood 196 in the reagent chamber 130, 130', 130", the reactive element 131, 131', 131" indicates a positive result by changing colors and/or producing a florescent glow to indicate (e.g., the changing color and/or fluorescent glow are shown as black dots in the chamber 130, 130', 130"). In an exemplary embodiment, the first responder is able to identify which drug has tested positive through the crystalline reagent 131 changing colors by checking the label 190a-190e located near the reagent chamber 130.

In another embodiment, the capillary force of the collecting tube 120 can be increased by the placement of a small wick 176 near the top button 180. In an embodiment, the small wick 176 is disposed in the top end of the collecting tube 120. In one embodiment, the small wick 176 acts with the capillary action of the hollow portion 125 of the collecting tube 120 and causes the process of filling up the entire hollow portion 125 to take a maximum of two seconds, for example. The small wick does 176 this by adding its absorptive "sponge-like" power to the suction power of the capillary force, which creates an even more powerful suction effect and increases the efficiency of device 100 even more. In one embodiment, the small wick 176 will be a cotton ball wick, which also absorbs the fluid as the fluid reaches the wick at the end of the hollow portion 125.

Figure 5:
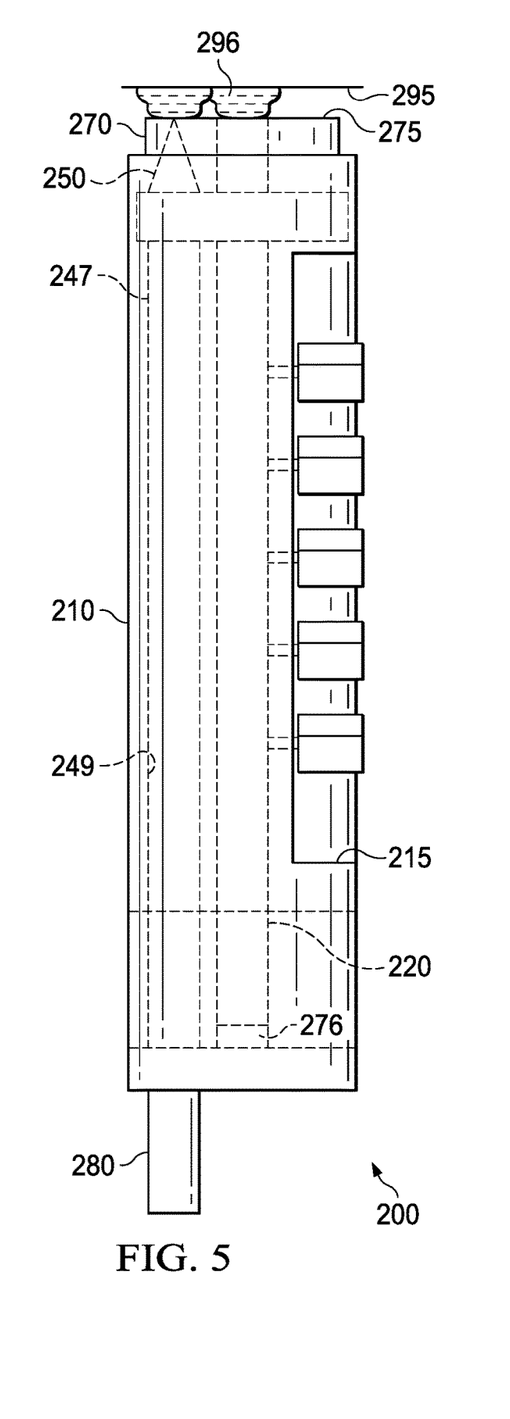
FIG. 5 is a partial broken-away side view of a drug detection device in which a stored lancet is disposed in a storage compartment within an outer casing, according to an exemplary embodiment.

FIG. 5 is still another example of a detection device 200. Certain components of the detection device 200 are as described above in connection with detection device 100, except as noted herein. Those components bear similar reference characters to the components of the detection device 100, but with a leading '2' rather than a leading '1'. The detection device 200 includes a stored lancet 247 disposed adjacent to the collection tube 220. A storage compartment 249 can be disposed in the outer casing 210 for receiving the stored lanced 247 therein. In an embodiment, the detection device 200 includes a lancet striker as described with detection device 100. In other embodiments, the button 280, pushes the stored lancet 247 directly downward to draw blood from the patient. In operation, the stored lancet is activated to draw blood from the patient, which, in some embodiments, opens the cover opening 275. In other embodiments, the cover opening 275 is removed by the user, which permits the lancet 250 to exit the device and the blood to enter the collecting tube 220.

Figure 6:
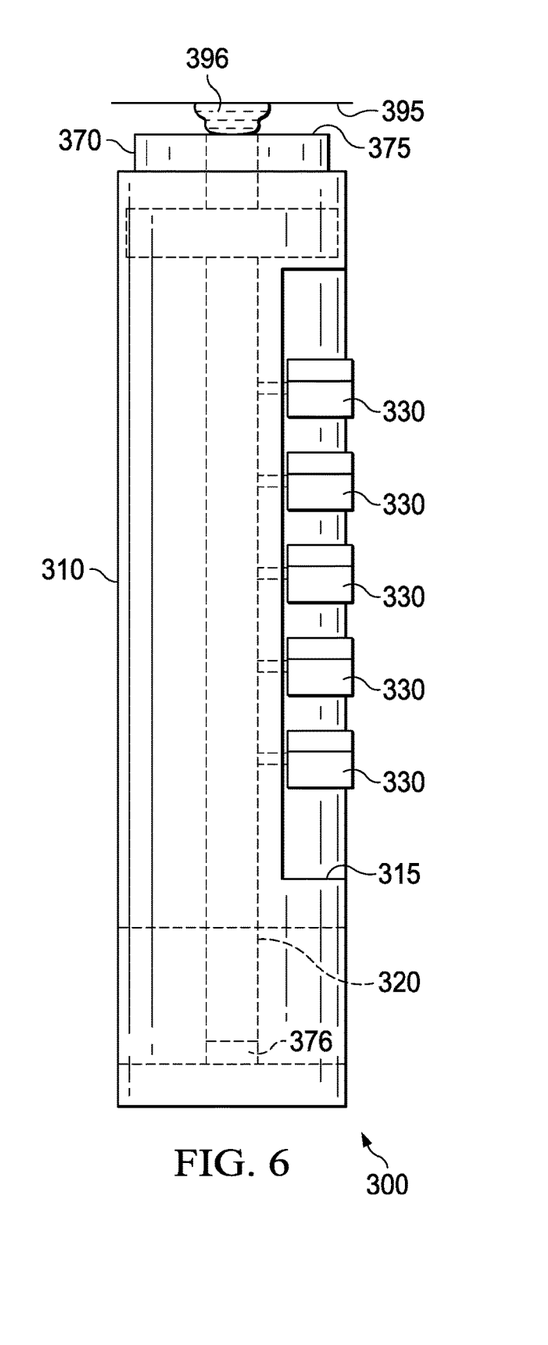
FIG. 6 is a partial broken-away side view of a drug detection device, according to an illustrative embodiment.

FIG. 6 is still another example of a detection device 300. Certain components of the detection device 300 are as described above in connection with detection device 100, except as noted herein. Those components bear similar reference characters to the components of the detection device 100, but with a leading '3' rather than a leading '1'. The detection device 300 does not include a lancet and simply uses drawn blood by conventional means. The cover opening 375 can be removed manually by the user to expose the collecting tube 320.

Embodiments of the drug detection device as described herein are advantageously suited for use in the field by first responders (e.g., there are no electronics in drug detection device that can break, no spectrum analysis or laboratory is needed for a positive result using the drug detection device). For example, if the drug, detection device is dropped in the field there are no electronics or complicated inner workings that will break. Moreover, since no electronics or electrical circuits are used in the drug detection device; there is no requirement for batteries (e.g., battery life is not a concern). In some embodiments, the drug detection device is waterproof.

Embodiments of the drug detection device can advantageously include a plurality of reagent chambers with a plurality of reactive elements. In an embodiment, each of the reactive elements in the plurality of reactive elements is different. For example, for a suspected drug overdose, the plurality of reactive elements can include tests for several different drugs to identify the cause of the overdose and possible combinations thereof. There can be an infinite number of combinations of the reactive elements for the drug detection devices envisioned herein. For example, but not limitation, the detection device can include a plurality of reactive elements (e.g., a panel of tests) in the reagent chambers for a particular type of diagnosis: a suspected illegal drug overdose detection device; a suspected over-the-counter drug overdose detection device; a suspected prescription drug overdose detection device; a child poisoning detection device; a venom detection device; a toxin detection device; and a biological weapon detection device. A first responder can run several detection devices to quickly diagnose a nonresponsive patient in the field (e.g., run an illegal drug overdose detection device, then a prescription drug overdose detection device, etc. until a positive result is achieved). The combination of the plurality of reactive elements can be selected for a particular geographic region (e.g., the venom detection device can focus on snakes and spiders located in southern states).

The particular embodiments disclosed above are illustrative only, as the device may be modified and practiced in different but equivalent manners apparent to those skilled in the art having the benefit of the teachings herein. Modifications, additions, or omissions may be made to the devices described herein without departing from the scope of the invention. The components of the device may be integrated or separated. Moreover, the operations of the device may be performed by more, fewer, or other components.

Furthermore, no limitations are intended to the details of construction, or design herein shown, other than as described in the claims below. It is therefore evident that the particular embodiments disclosed above may be altered or modified and all such variations are considered within the scope and spirit of the application. Accordingly, the protection sought herein is as set forth in the claims below.

It may be advantageous to set forth definitions of certain words and phrases used in this patent document. The terms "a" and "an" are defined as one or more unless this disclosure explicitly requires otherwise.

The term "substantially" is defined as largely, but not necessarily wholly, what is specified (and includes what is specified; e.g., substantially 90 degrees includes 90 degrees), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The term "plurality" can mean "at least one". The phrases "associated, with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Terms such as "first", "second", "primary", and "secondary" are used only to differentiate features and not to limit the different features to a particular order, importance, or quantity.

What is claimed is:

1. A device for detecting a substance within blood, comprising:
    a collecting tube dimensioned to draw in blood through capillary action;
    a plurality of reagent chambers;
    a plurality of reactive elements, each reagent chamber containing one of the plurality of reactive elements, wherein each reactive element is configured to react to one of a plurality of substances; and
    a plurality of connector tubes configured to provide fluid communication between each of the reagent chambers and the collecting tube, each connector tube corresponding to one of the reactive elements;
    wherein each of the plurality of connector tubes has a diameter smaller than a diameter of the collecting tube and is dimensioned to draw in blood through capillary action from the collecting tube to each of the reagent chambers; and
    wherein each of the plurality of reactive elements comprises individual crystals that are larger than the diameter of a corresponding connector tube to prevent backflow.

2. The device according to claim 1, wherein each reactive element is configured to react to one of the plurality of substances as part of an immunoassay.

3. The device according to claim 1, wherein each of the plurality of reactive elements is configured to provide a visible change within one of the reagent chambers that indicates a positive reaction to one of the plurality of substances.

4. The device according to claim 3, wherein the visible change is a change in color.

5. The device according to claim 3, wherein the visible change is a fluorescent glow.

6. The device according to claim 1, wherein each of the plurality of reactive elements is secured to an inner surface of each of the reagent chambers.

7. The device according to claim 6, wherein each reagent chamber comprises a top inner surface, and each of the reactive elements is secured to the top inner surface of one of the reagent chambers.

8. The device according to claim 1, wherein each of the reagent chambers is at least one of the following shapes: a cylinder and a cuboid.

9. The device according to claim 1, wherein the one of the plurality of substances comprises at least one of: a drug, an active ingredient in a drug, an illicit drug, a narcotic drug, a prescription drug, and over-the-counter drug, opium, tetrahydrocannabinol, synthetic cannabinoids, K2, phencyclidine, gaseous intoxication, toxins, alcohol, venom, amphetamine, lysergic acid diethylamide, acetaminophen, a hazardous chemical, a household chemical, a hazardous plant, a chemical weapon, a biological illness, a biological disease, or a biological weapon.

10. A device for detecting a substance within blood, comprising:
an outer casing;
a collecting tube dimensioned to draw in blood through capillary action;
a plurality of reagent chambers;
a plurality of reactive elements, each reagent chamber containing one of the plurality of reactive elements, wherein each reactive element is configured to react to one of a plurality of substances; and
a plurality of connector tubes configured to provide fluid communication between each of the reagent chambers and the collecting tube, each connector tube corresponding to one of the reactive elements;
wherein each of the plurality of connector tubes has a diameter smaller than a diameter of the collecting tube and is dimensioned to draw in blood through capillary action from the collecting tube to each of the reagent chambers; and
wherein each of the plurality of reactive elements comprises individual crystals that are larger than the diameter of a corresponding connector tube to prevent backflow.

11. The device according to claim 10, wherein the outer casing comprises an opening located so that the reagent chamber is viewable.

12. The device according to claim 10, further comprising:
a label proximate to the reagent chamber, the label configured for identifying a visible change in the reagent chamber that identifies a positive reaction to the substance.

13. The device according to claim 10, further comprising:
a hollow lancet disposed on an entry opening of the collecting tube;
wherein the hollow lancet is configured to be selectively advanced and retracted to draw blood from a patient into the collecting tube.

14. The device according to claim 10, further comprising:
a stored lancet disposed in the outer casing;
wherein the stored lancet is configured to be selectively advanced and retracted using a spring to draw blood from a patient.

15. The device according to claim 14, further comprising:
a stored lancet storage compartment disposed in the outer casing.

16. The device according to claim 10, further comprising:
a wick located within a top end of the collecting tube.

17. The device according to claim 10, wherein the visible change is a fluorescent glow.

18. The device according to claim 10, wherein the one of a plurality of substances is at least one of: a drug, an active ingredient in a drug, an illicit drug, a narcotic drug, a prescription drug, an over-the-counter drug, opium, tetrahydrocannabinol, synthetic cannabinoids, K2, phencyclidine, gaseous intoxication, toxins, alcohol, venom, amphetamine, lysergic acid, diethylamide, acetaminophen, a hazardous chemical, a household chemical, a hazardous plant, a chemical weapon, a biological illness, a biological disease, or a biological weapon.

19. A device for detecting a plurality of different substances within blood, comprising:
an outer casing;
a collecting tube disposed in the outer casing, the collecting tube dimensioned to draw in blood through capillary action;
a plurality of reagent chambers;
a plurality of reactive elements, each reagent chamber containing a different one of the plurality of reactive elements, wherein each reactive element is configured to provide a visible change in the reagent chamber that identifies a positive reaction to one of the plurality of different substances; and
a plurality of connector tubes configured to provide fluid communication between each of the plurality of reagent chambers and the collecting tube, each connector tube corresponding to one of the reactive elements;
wherein each of the plurality of connector tubes has a diameter smaller than a diameter of the collecting tube and is dimensioned to draw in blood through capillary action from the collections tube to each of the reagent chambers; and
wherein each of the plurality of reactive elements comprises individual crystals that are larger than the diameter of a corresponding connector tube to prevent backflow.

20. The device according to claim 1, wherein the reactive element in each of the plurality of reagent chambers is different.

21. The device according to claim 19, wherein the plurality of different substances is at least one of: a drug, an active ingredient in a drug, an illicit drug, a narcotic drug, a prescription drug, an over-the-counter drug, opium, tetrahydrocannabinol, synthetic cannabinoids, K2, phencyclidine, gaseous intoxication, toxins, alcohol, venom, amphetamine, lysergic acid diethylamide, acetaminophen, a hazardous chemical, a household chemical, a hazardous plant, a chemical weapon, a biological illness, a biological disease, or biological weapon.

* * * * *